(12) United States Patent     (10) Patent No.: US 12,569,272 B2

Gryshchuk     (45) Date of Patent: Mar. 10, 2026

---

(54) METHOD FOR RADIOFREQUENCY RESECTION OF MENISCUS AND ARTHROSCOPIC INSTRUMENT FOR IMPLEMENTATION THEREOF (VARIANTS)

(71) Applicant: Bogdan Yaroslavovych Gryshchuk, Kyiv (UA)

(72) Inventor: Bogdan Yaroslavovych Gryshchuk, Kyiv (UA)

( * ) Notice: Subject to any disclaimer, the term of this patent is extended or adjusted under 35 U.S.C. 154(b) by 885 days.

(21) Appl. No.: 17/627,742

(22) PCT Filed: Jul. 17, 2020

(86) PCT No.: PCT/UA2020/000071
§ 371 (c)(1),
(2) Date: Jan. 17, 2022

(87) PCT Pub. No.: WO2021/010936
PCT Pub. Date: Jan. 21, 2021

(65) Prior Publication Data
US 2022/0257275 A1     Aug. 18, 2022

(30) Foreign Application Priority Data

| Jul. 18, 2019 | (UA) | ............................... | u 2019 08572 |
| Nov. 1, 2019 | (UA) | ............................... | u 2019 10838 |
| Jul. 16, 2020 | (UA) | ............................... | u 2020 04428 |

(51) Int. Cl.
    *A61B 17/32*     (2006.01)
    *A61B 17/3205*     (2006.01)
         (Continued)

(52) U.S. Cl.
    CPC .......... *A61B 17/3205* (2013.01); *A61B 17/56* (2013.01); *A61B 18/14* (2013.01)

(58) Field of Classification Search
    CPC ................ A61B 17/3205; A61B 17/56; A61B 2017/00367; A61B 18/14; A61B 18/148; A61B 18/149; A61B 2018/00565; A61B 2018/00601; A61B 2018/0091; A61B 2018/00922; A61B 2018/00982; A61B 2018/1253; A61B 2018/126; A61B 2018/1407; A61B 2018/1475; A61B 2217/005; A61B 2218/007

See application file for complete search history.

(56) References Cited

U.S. PATENT DOCUMENTS

| 4,203,444 A | 5/1980 | Bonnell et al. |
| 5,658,280 A | 8/1997 | Issa |
| | | (Continued) |

FOREIGN PATENT DOCUMENTS

| EP | 0715504 | 6/1996 |
| WO | WO2018182836 | 10/2018 |

*Primary Examiner* — Khadijeh A Vahdat

(74) *Attorney, Agent, or Firm* — Defillo & Associates, Inc.; Evelyn A. Defillo

(57) ABSTRACT

A device for carrying out arthroscopic operations on the knee joints. The device includes handle, a proximal axial rotation control, and a distal linear movement control, a drainage tube and a power cable are connected to the proximal end, and extending from the distal end is an inner tube having an opening into which an electrode loop is inserted, and further having an aspiration opening oriented into a drainage channel.

4 Claims, 11 Drawing Sheets

(51) Int. Cl.
    *A61B 17/56*       (2006.01)
    *A61B 18/14*       (2006.01)

(56)            References Cited

U.S. PATENT DOCUMENTS

| | | | | |
|---|---|---|---|---|
| 5,810,764 | A | 9/1998 | Eggers et al. | |
| 7,837,683 | B2 | 11/2010 | Carmel et al. | |
| 2003/0014047 | A1* | 1/2003 | Woloszko | A61B 18/149 |
| | | | | 606/41 |
| 2003/0181906 | A1 | 9/2003 | Boebel et al. | |
| 2003/0225403 | A1 | 12/2003 | Woloszko et al. | |
| 2004/0002746 | A1* | 1/2004 | Ryan | A61B 18/14 |
| | | | | 607/99 |
| 2008/0188711 | A1 | 8/2008 | Eliachar | |
| 2009/0030431 | A1 | 1/2009 | Zaporojan et al. | |
| 2009/0171147 | A1 | 7/2009 | Lee | |
| 2011/0295066 | A1 | 12/2011 | Fan | |
| 2014/0236143 | A1 | 8/2014 | Ward | |
| 2015/0216585 | A1 | 8/2015 | Kirstgen et al. | |
| 2017/0273709 | A1 | 9/2017 | Sakamoto et al. | |
| 2017/0280988 | A1* | 10/2017 | Barbato | A61B 1/317 |

* cited by examiner

1

METHOD FOR RADIOFREQUENCY RESECTION OF MENISCUS AND ARTHROSCOPIC INSTRUMENT FOR IMPLEMENTATION THEREOF (VARIANTS)

CROSS REFERENCE TO RELATED APPLICATION

This application is a national stage entry of PCT/UA2020/000071 filed Jul. 17, 2020, under the International Convention and claiming priority over Ukraine Patent Application No. u 2019 08572 filed Jul. 18, 2019; Ukraine Patent Application No. u 2019 10838 filed Nov. 1, 2019; and Ukraine Patent Application No. u 2020 04428 filed Jul. 16, 2020.

FIELD OF THE INVENTION

The invention relates to medicine, in particular to medical equipment, namely, to instruments and methods for performing resections of joint tissues, and it can be used when carrying out surgeries on joints, for instance, knee ones.

BACKGROUND OF THE INVENTION

There is a known surgical arthroscopic method, comprising: an identifying step of identifying a damage site of a meniscus an administering step of administering a fluorescent agent to a vein, a confirmation step of confirming whether the damage site reaches a vascular area in an inside of the meniscus, by performing, after the administering step, fluorescence observation by causing the fluorescent agent to emit fluorescence with the use of near-infrared light, and when the damage site does not reach the vascular area in the confirmation step, a setting step of forming, an inclined surface such that a resection target area includes the damage site, and an inclination of the inclined surface increases from a central side toward an outside of the curved shape, and setting a boundary of the resection target area within a no-vascular area of the meniscus. According to this method, the resection procedure y is performed with an ultrasonic instrument [US 2017/0273709 A1, A61B 17/32, A61B 17/00, 2017].

The disadvantages of this method are as follows:

Because of the availability of the confirmation step and the setting step of forming the resection target area, the duration of the surgical intervention is increased.

The ultrasonic instrument is not able to carry out the procedure of coagulation to stop bleeding if it occurs.

The ultrasonic method of resection creates an area of ultrasonic vibration that spreads deep into the tissues and can cause additional trauma.

In addition, the disadvantage is the need for the step of administering a fluorescent agent and the probability of an allergic reaction to it.

The method is energy consuming, more traumatic and expensive.

There is also a known method for resection of meniscus using a system of arthroscopic instruments, wherein after standard treating procedures of preparation and processing, arthroscopic ports are installed in a knee joint, into one of the ports, an arthroscopic cutting device is inserted, the damage site of the meniscus is identified and its resection and evacuation are carried out, then the instrument is removed and the wounds are sutured [US 2017/0280988 A1, Devices and Methods for Minimally Invasive Surgery, VISION-SCOPE TECH LLC, US, 5 Oct. 2017].

However, to implement this method, a large number of cutting devices are required. There is a need in their replacement, since the cutting devices tend to become blunt and fail. Moreover, it is necessary to sterilize the cutting devices, which fact additionally increases the costs (for sterilization consumables) and complicates the preparation for surgery (wasting extra time for sterilization).

There is a known method for resection of meniscus using a system of arthroscopic instruments, wherein, after resection, a dissected fragment of the meniscus is evacuated using a medical clamp or other suitable tool [US 2009/0030431 A1, ZIMMER ORTHOBIOLOGICS INC, US, Jan. 29, 2009].

However, this method uses the technology of electrocautery for meniscus resection procedure (sectioning of biological tissue), which causes thermal burns of the tissue and, as a consequence, its necrotization. That is, this method is more traumatic for the whole tissue.

The closest to the claimed method is a method of treating joint tissues, which includes removing injured tissue from the target area using a tool, where a plurality of active electrodes are placed close to the target tissue, supplying them with radio frequency energy sufficient to destroy tissue using localized molecular dissociation of tissue components. Via (the end of Page 1.1) an aspirating device, which is attached to the instrument, it is possible to efficiently remove unwanted materials, including tissue fragments, from the target area, and provide a relatively smooth and uniform contoured tissue. During the procedure, the liquid, not destroyed tissue fragments and/or air bubbles occur removed from the target area to improve visualization [US 2003\0225403 A1, A61 B 18/14, 2003].

The disadvantages of this method are the followings

At the distal end of the instrument, there is a large number of active electrodes, which while operating cause the process of a sufficiently large area tissue ablation, in turn, not allowing to make an accurate cut of the "target tissue" and resulting in excessive damage to the surrounding tissues;

In addition, in the course of the ablation process, there appear many small fragments of various sizes and shapes, which need to remove from the joint by an aspiration channel. Because of a large number thereof, there is a risk that not all of those small fragments would pass through the aspiration channel and some of them remain in the joint. In this case, there is also a risk of blocking the canal with the large fragments, which issue requires additional electrodes to destroy them.

There is a known arthroscopic surgical instrument comprising a hollow tube with its proximal end and its distal end, which consists of its stationary part and its movable one configured to form a toothed surface. The proximal end comprises a stationary handle and a movable one. The movable handle is associated with the pushing rod connected to the movable part of the distal end. When operating the movable handle, the pushing rod actuates the movable part of the distal end with forcing it to move towards the stationary part of the distal end. As a result, a cutting action occurs between the sharp edges of the distal end. The instrument can perform the function of cauterization with the help of an electrical connector passing through a driving device to the tube for providing the possibility of supplying electric current thereto [EP0715504B 1, A61 B 17/32, 1995].

This instrument has the following disadvantages:

Mechanical tissue resection is more traumatic for tissues than radiofrequency resection.

As a result of mechanical tissue resection, dissected tissues circulate in a joint cavity, which affects visualization and forces the use of additional resources for the removal of resection products, namely, tissues, from a joint cavity.

There is a known arthroscopic instrument for executing a tissue ablation by an aspiration electrode with the use of a cable connected to an electric generator that transmits energy to the electrode, and with the help of a tube associated with a vacuum pump to provide an operation of a drainage system. To control the energy transfer to the electrode, the handle of the instrument has two buttons specified as "ablation" and "coagulation". The operating part of the instrument comprises a tube with an electrode at the end thereof. In the course of transferring energy to the electrode, there appears a "vapor pocket", which causes the tissue vaporization therein. The instrument is designed for performing volumetric removal of tissue by evaporating thereof. The electrode contains a drainage hole, which ensures outflowing liquid and vaporization products from the joint cavity through a conductive system coming out of the distal end of the handle. The above said electrodes are used in a medium filled with an electrically conductive liquid [U.S. Pat. No. 7,837,683B, A61B18/18 2007].

The instrument makes it possible to vaporize a large volume of tissue, but it does not allow carrying out high-precision tissue resections, the operating part thereof is stationary, and the electrode is unchangeable. The instrument operation requires a return electrode applied to the patient's body.

There is a known endoscopic instrument, which uses a loop electrode to carry out radiofrequency resections. The instrument comprises an outer tube configured to insert into the patient's body through an incision in the patient's tissues and an inner tube provided with a telescope and a loop-electrode. The above said instrument comprises a manipulator designed for carrying out a linear movement of the loop-electrode from a closed position inside the outer tube to an open (operating) position, in which the loop-electrode protrudes beyond the outer tube, and an axial rotation manipulator for rotating the inner tube and the loop-electrode in the course of the operation. [US 2011/0295066 AI, FAN TAILIN, US, GYRUS ACMI INC, US, Jan. 12, 2011].

This instrument disadvantages are as follows:

Made with the possibility of repeated use, its complex design requires manual cleaning of many parts of the instrument, as well as their sterilization.

The presence of a telescope as a part of the structure significantly increases the diameter of the instrument distal end intended to insert into the human body cavity. Therefore, it is not practicable to use it in the cavity of a human knee joint, because its compartment average height is 5 mm. This makes it impossible to access the knee meniscus. That is, this instrument usage for knee meniscus resection is out of the question.

In addition, known is a resection and ablation surgical instrument connected to an energizer and a drainage system. The instrument comprises a handle with a power cable and a drain tube connected thereto. An inner tube, which is an aspiration channel with a loop-electrode and a telescope arranged therein, runs out from the distal end of the handle. To supply power to the loop-electrode, the instrument is provided with a pedal switch [U.S. Pat. No. 5,810,764 A, ARTHROCARE CORP, US, 22 Sep. 1998].

However, this instrument disadvantages are as follows:

Made with the possibility of repeated use, its complex design requires manual cleaning of many parts of the instrument, as well as their sterilization.

The presence of a telescope as a part of the structure significantly increases the diameter of the instrument distal end formed to insert into the human body cavity. Therefore, it is not practicable to use it in the cavity of a human knee joint, because its compartment average height is 5 mm. This makes it impossible to access the knee meniscus. That is, this instrument usage for knee meniscus resection is out of the question.

To advance the loop-electrode, it is necessary to execute a linear movement of the inner tube of the instrument, while in order to fix it in the specified position, it is obligatory to keep the manipulator jaws clamped, which requires additional efforts that is, in this instrument, it is impossible to fix the loop-electrode outside the outer tube.

The closest to the claimed invention is an endoscopic instrument for operations in gynecology and andrology, namely, a resectoscope, consisting of a handle and an operating part. The operating part of the resectoscope comprises an inner tube provided with an electrode, an outer tube configured with holes for irrigation, locks of the tubes formed for supplying current thereto. The handle consists of two jaws with a mechanism for driving the inner tube, and the locks to which a fluid feeder and an optical device are connected. With the help of a pedal switch connected to a console, there it occurs current supply to the electrodes connected to the locks of the resectoscope operating part. At the jaws of the handle clamped, the inner tube, while moving, executes the procedure of tissue resection enabled with high-frequency current. The optical device provides the visualization of the operating field. The drainage system ensures the circulation of fluid in the operating field [U.S. Pat. No. 5,658,280, A61 B 17/39, 1995].

Such a resectoscope has a rather complex design (the presence of optical system, irrigation systems, obturator, etc.), a limited trajectory for carrying out the procedure of a resection, which provides only a linear movement of the electrodes. Due to the arrangement of the optical system inside, the resectoscope has a rather large diameter not allowing using it as an arthroscopic instrument.

SUMMARY OF THE INVENTION

The invention is based on the technical problem of creating a method for radiofrequency resection of meniscus, which would increase the accuracy of the resection procedure, improve visualization in the course of surgical interference, reduce the level of joint tissue trauma, increase the resource of surgical support for arthroscopic operations and shorten timing of surgery (The end of Page 3. 2).

The second technical problem having been set in the basis of the invention is the creation of an arthroscopic instrument for radiofrequency resection of meniscus, which would contribute to the accuracy of resection procedure and reduce operating time.

The first technical problem is solved by the fact that in the method for radiofrequency resection of meniscus, which is carried out by a system of arthroscopic devices comprising an optical arthroscope and a radiofrequency energizer suitable for connection to an arthroscopic cutting instrument, while at least two arthroscopic ports are set into the knee joint being treated, the optical arthroscope is inserted into one of the said arthroscopic ports, an area of the meniscus damage is identified, then the arthroscopic cutting instrument is inserted into the said knee joint through the other of the said arthroscopic ports, the identified area of the meniscus damage is excised and evacuated from the above said knee joint, and the wounds are sutured, according to the claimed invention, the identified area of the meniscus damage is excised using the arthroscopic cutting instrument for radiofrequency resection of meniscus comprising an outer tube, an inner tube with a loop-electrode rigidly installed into the inner tube, and a handle provided with a starting device and a distal manipulator for the outer tube linear movement, in this case, the above said outer tube with the inner tube fixed therein is inserted into the knee joint being treated when the outer tube is in its closed position, then while transferring the outer tube into the open position thereof, the meniscus resection procedure is carried out, on the resection procedure completion, the outer tube is returned to its closed position, and then it is taken from the knee joint, further the excised fragment of the meniscus is evacuated from the knee joint using an arthroscopic clamp, wherein transferring the outer tube with the inner tube fixed therein from the closed position to the open position and the reverse is carried out at linearly moving the outer tube with the use of the distal manipulator.

In the variant of the proposed method, the resection of the damaged meniscus area is carried out with an arthroscopic cutting instrument, in which the inner tube is installed in the outer tube with the possibility of axial rotation inside the outer tube, while this axial rotation being carried out with the use of the proximal manipulator additionally mounted on the handle of the arthroscopic instrument for radiofrequency resection of the meniscus. At the same time, when moving the outer tube to the open position thereof, the meniscus resection procedure is performed with additionally imparting axial rotation to the inner tube with the loop-electrode fixed in it, moreover, transferring the outer tube with the above said inner tube, installed therein with the possibility of axial rotation, from the outer tube closed position to the open position thereof and the reverse is carried out at linearly moving of the outer tube with the use of the distal manipulator together with carrying out the axial rotation of the inner tube with the loop-electrode rigidly installed therein with the use of the proximal manipulator.

The second technical problem is solved due to the creation of an arthroscopic instrument for radiofrequency resection of meniscus, which is connected to an energizer and a drainage system and comprises a handle with a "start" button located on it, while at the handle distal end, an outer tube with an inner tube inside it is arranged, the inner tube has an aspiration opening and an opening formed to install a loop-electrode therein, and at the above said handle proximal end, there is a drainage tube and a power cable, which are connected thereto, wherein in compliance with the claimed invention, the loop-electrode is rigidly installed in the inner tube, the above said inner tube is fixed inside the outer tube, which is configured to be linearly displaced inside the handle distal end by a distal manipulator arranged on the above said handle, and the outer tube diameter is not more than 5 mm.

In the variant of the proposed instrument, the inner tube with the loop-electrode rigidly installed therein is configured to be axially rotated inside the outer tube by a proximal manipulator also arranged on the handle of the claimed instrument.

The variant of the claimed instrument has a wider functionality due to the ability to provide the inner tube and a loop-electrode, fixedly installed in it, with axial rotation thereof, using a proximal manipulator located on the handle of the instrument.

The cutting loop-electrode of the arthroscopic instrument allows carrying out the process of high-precision tissue resection with minimal trauma. Operating with such a loop-electrode makes it possible to achieve a smooth and even resection line. Due to this fact, there is no need for additional tissue processing. Unlike the prototype, this instrument prevents the emergence of a large number of small tissue resection products that impair the visualization of the surgical field. Microscopic products occur removed through draining devices, while macroproducts evacuated with an arthroscopic clamp or using a shaver system.

The presence of the manipulators for executing linear movement and rotation around the axis by the operating inner tube with a loop-electrode installed therein facilitates the instrument operation and reduces the duration of the surgical intervention.

The arthroscopic instrument for radiofrequency resection of the meniscus allows preserving the beneficial surface properties of individual joint tissues after processing them.

The claimed method is cost-effective due to an increase in the resource of surgical support for arthroscopic operations (there is no need to use an arthroscopic cutting device), economy of time, duration of anesthesia, and providing comfortable operation conditions for the surgeons.

BRIEF DESCRIPTION OG THE DRAWINGS

The essence of the invention is illustrated by the following figures.

DETAILED DESCRIPTION OF THE INVENTION

Figure 1:
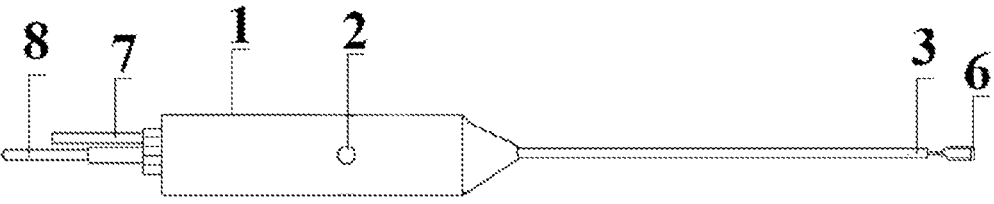
FIG. 1 shows the arthroscopic instrument for radiofrequency resection of the meniscus in the first embodiment.
Figure 2:
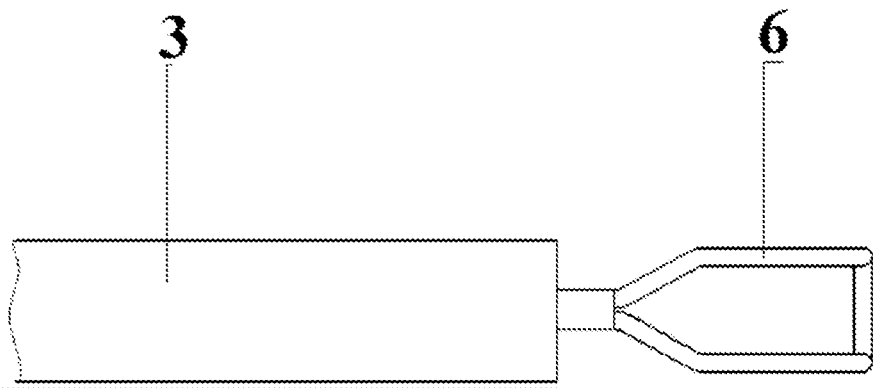
FIG. 2 shows the distal end of the arthroscopic instrument for radiofrequency resection of the meniscus in the first embodiment, the top view.
Figure 3:
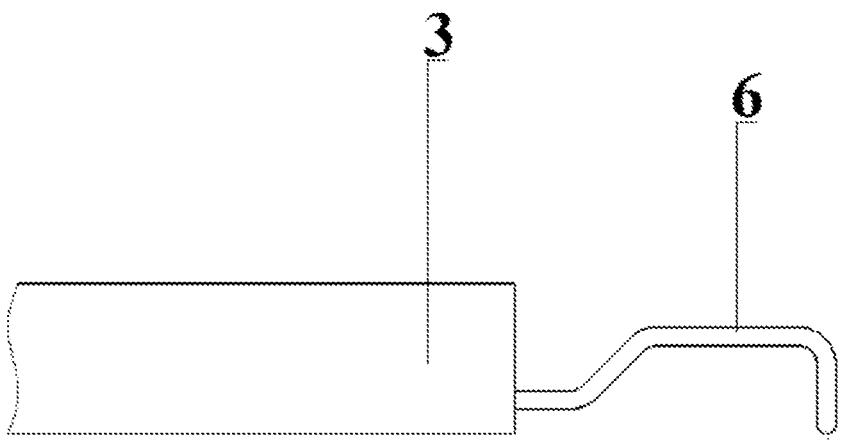
FIG. 3 shows the distal end of the arthroscopic instrument for radiofrequency resection of the meniscus in the first embodiment, the side view.
Figure 4:
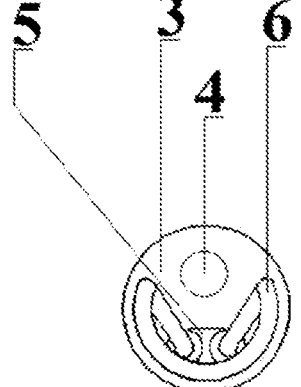
FIG. 4 shows the distal end of the arthroscopic instrument for radiofrequency resection of the meniscus in the first embodiment, the front view.
Figure 5:
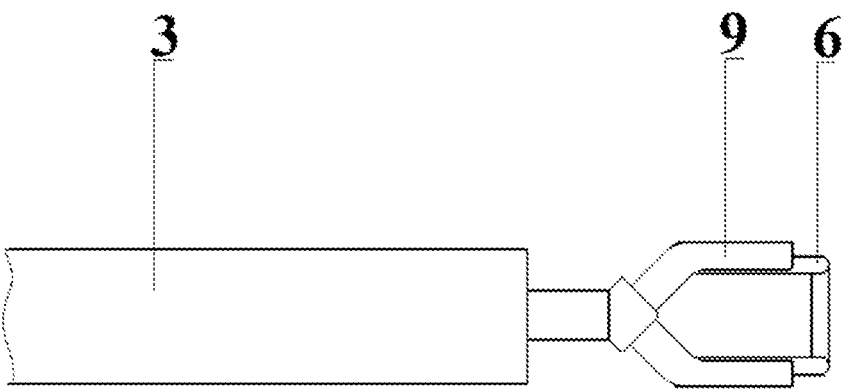
FIG. 5 shows the distal end of the arthroscopic instrument for radiofrequency resection of the meniscus in the first embodiment with an aspiration tube, the top view.
Figure 6:
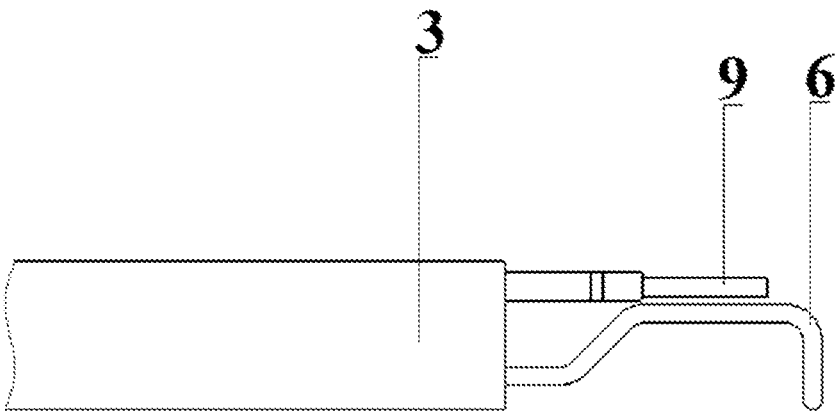
FIG. 6 shows the distal end of the arthroscopic instrument for radiofrequency resection of the meniscus in the first embodiment with an aspiration tube, the side view.
Figure 7:
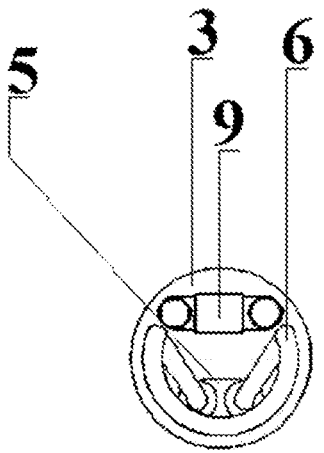
FIG. 7 shows the distal end of the arthroscopic instrument for radiofrequency resection of the meniscus in the first embodiment with an aspiration tube, the front view.

The first embodiment (FIG. 1) of the claimed arthroscopic instrument consists of handle 1 having "start" button 2 on the surface thereof, at the distal end of the handle, there is inner tube 3 extending therefrom. The above said inner tube has aspiration opening 4 and opening 5 with changeable loop-electrode 6 arranged therein. The handle has drainage tube 7 and power cable 8 attached to the proximal end thereof. To improve the removal of bubbles arising during operation, aspiration tube 9 can be additionally set into aspiration opening 4 in a position adjacent to the electrodes of loop-electrode 6, which fact, in turn, improves visualization of the surgical area. At the same time, the diameter of the inner tube does not exceed 5 mm, making it possible to carry out actions in a narrow joint cavity. The arthroscopic instrument is connected to a radiofrequency energizer (not shown), which, in turn, is connected to a public main having a voltage of 100 to 220 V. The arthroscopic instrument operates in conductive solutions. In most cases, for joint surgery, 0.9% NaCl is used.

The arthroscopic instrument is made of materials that are resistant to temperature, corrosion and abrasion. The materials in contact with energy-conducting elements are dielectrics.

Handle 1 and inner tube 3 can be made of either plastic or metal, and they can be made both single-use and suitable for re-sterilization and reutilization.

The arthroscopic instrument can be made in a monopolar configuration, further requiring the use of a return electrode that is placed in contact with the patient's body.

Figure 8:
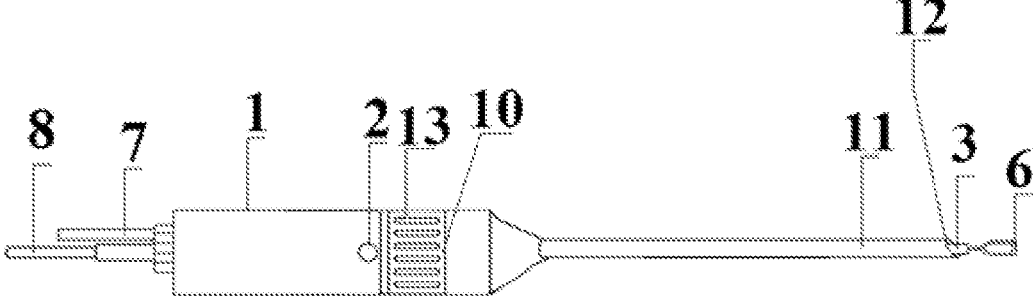
FIG. 8 shows the arthroscopic instrument for radiofrequency resection of the meniscus in the first variant.

In the first variant (FIG. 8), the arthroscopic instrument comprises distal manipulator 10 of linear motion, which is arranged on handle 1 distal of "start" button 2, and outside inner tube 3, there is outer tube 11 with tip 12 beveled at an angle.

Figure 11:
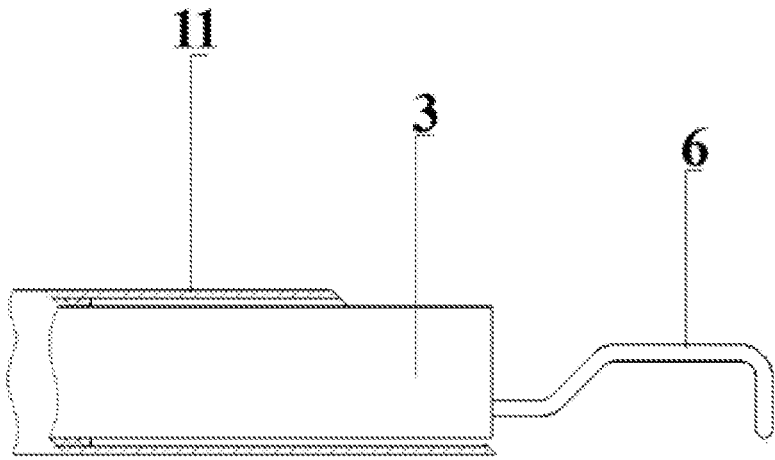
FIG. 11 shows the distal end of the arthroscopic instrument for radiofrequency resection of the meniscus in the first and second variants in the open position, the side view.
Figure 12:
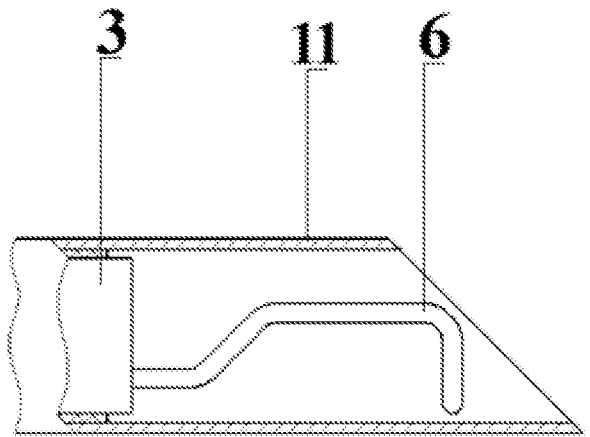
FIG. 12 shows the distal end of the arthroscopic instrument for radiofrequency resection of the meniscus in the first and second variants in the closed position, the side view.
Figure 13:
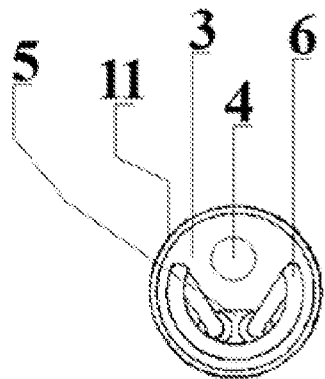
FIG. 13 shows the distal end of the arthroscopic instrument for radiofrequency resection of the meniscus in the first and second variants, the front view. (This is Replacement Page 6).
Figure 14:
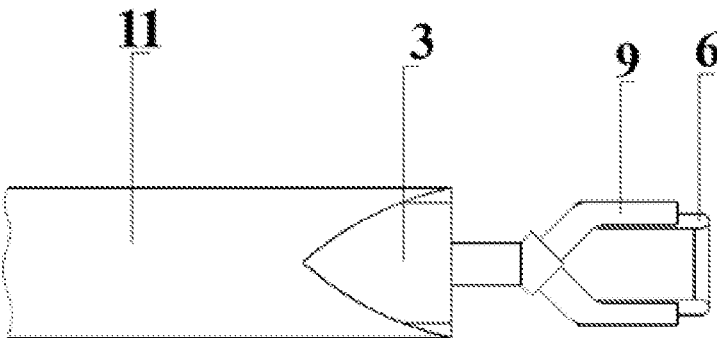
FIG. 14 shows the distal end of the arthroscopic instrument for radiofrequency resection of the meniscus in the first and second variants with an aspiration tube, the top view.
Figure 15:
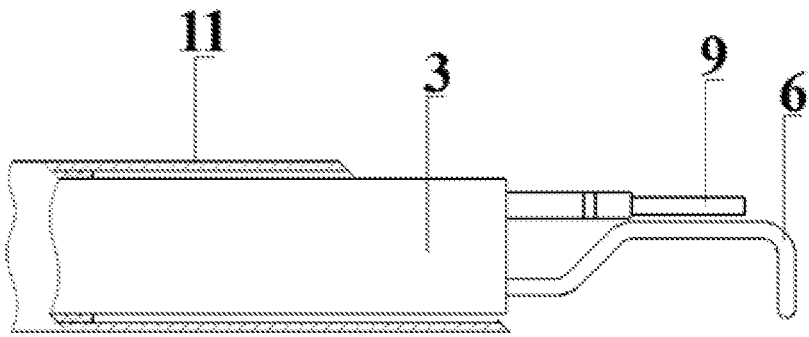
FIG. 15 shows the distal end of the arthroscopic instrument for radiofrequency resection of the meniscus in the first and second variants with an aspiration tube, the side view, in the open position
Figure 16:
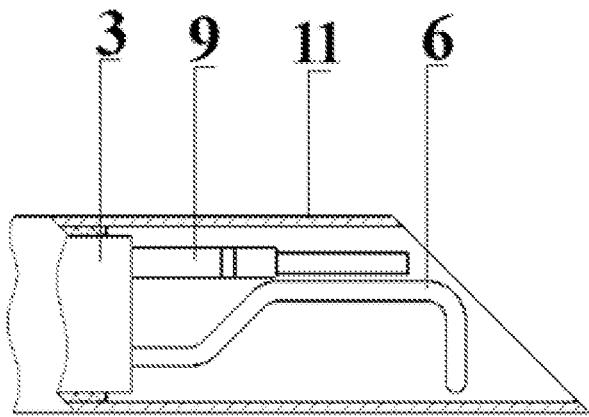
FIG. 16 shows the distal end of the arthroscopic instrument for radiofrequency resection of the meniscus in the first and second variants with an aspiration tube, the side view, in the closed position.
Figure 17:
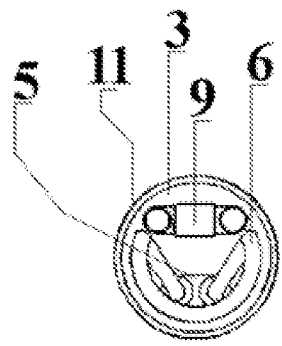
FIG. 17 shows the distal end of the arthroscopic instrument for radiofrequency resection of the meniscus in the first and second variants with an aspiration tube, the front view.
Figure 18:
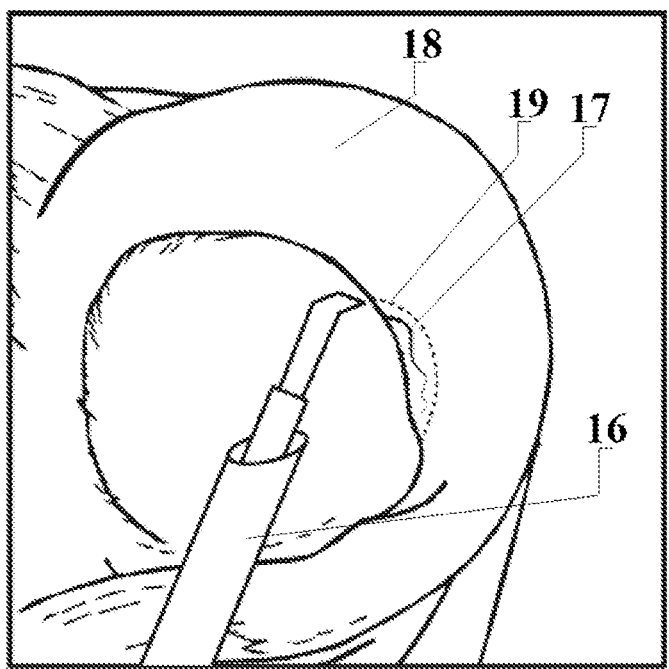
FIG. 18 shows the arthroscopic instrument for radiofrequency resection of the meniscus in the first and second variants in the open position, which is located in the cavity of the knee joint and arranged close to the damaged area of the meniscus.
Figure 19:
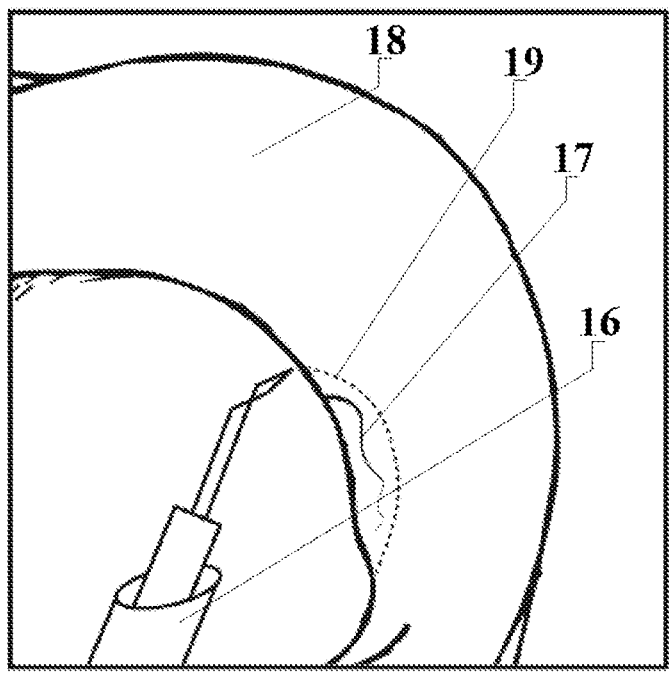
FIG. 19 shows the arthroscopic instrument for radiofrequency resection of the meniscus in the first and second variants in the open position, rotated 90 degrees to the right, which is located in the joint cavity and arranged close to the damaged area of the meniscus.

Outer tube 11 can be set in its open position (FIG. 11, FIG. 15) and in its closed one (FIG. 12, FIG. 16). When in closed position, outer tube 11 externally covers inner tube 3, which contains loop-electrode 6 therein, and protects the joint tissue and loop-electrode 6 itself from damage. When in the open position, inner tube 3 and loop-electrode 6 protrude from the outer tube sufficiently for ensuring full access to the "target tissue".

Tip 12 of outer tube 11 has a configuration beveled at an angle of 30 to 60 degrees, thereby reducing trauma at introducing the arthroscopic instrument into a joint cavity. At the same time, the diameter of the outer tube does not exceed 5 mm, making it possible to carry out actions in a narrow joint cavity.

The surface of distal manipulator 10 can be made with stiffening ribs 13 to improve the strength of the contact with the surgeon's hand and increase comfort when working with such an instrument.

Distal manipulator 10 can be made of both plastic and metal, which are resistant to temperature, corrosion and abrasion.

Figure 9:
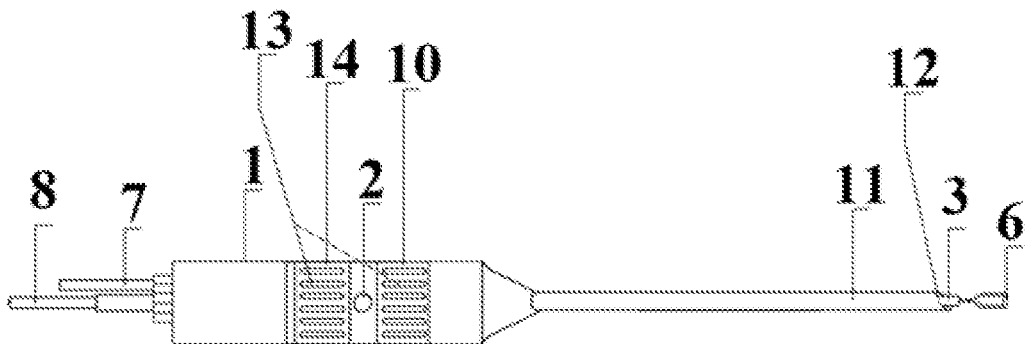
FIG. 9 shows the arthroscopic instrument for radiofrequency resection of the meniscus in the second variant.
Figure 10:
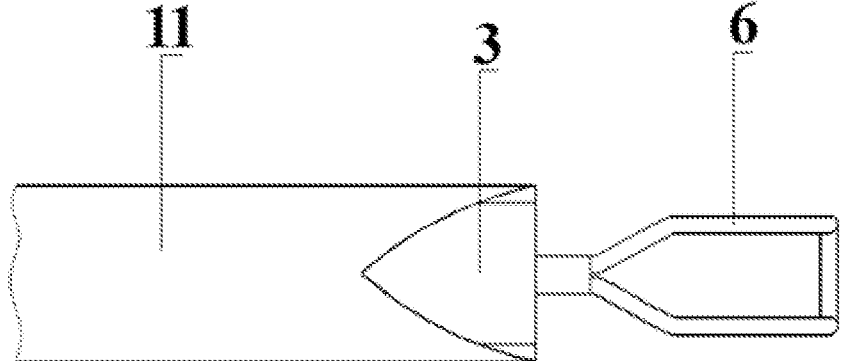
FIG. 10 shows the distal end of the arthroscopic instrument for radiofrequency resection of the meniscus in the first and second variants, the top view.

In the second variant (FIG. 9), on handle 1, proximal of "start" button 2, the arthroscopic instrument comprises proximal manipulator 14 to provide axial rotation of inner tube 3. Using the above said manipulator, a surgeon provides for rotation of inner tube 3 containing loop-electrode 6 around its axis. This, in turn, increases the functionality of the arthroscopic instrument, ensuring the possibility to monitor and control a cutting line and create comfortable conditions when using such an instrument.

Proximal manipulator 14 can be made of both plastic and metal, which are resistant to temperature, corrosion and abrasion.

The surface of proximal manipulator 14 can be configured to have stiffening ribs 13 to improve the strength of the contact with a surgeon's hand and increase the comfort when working with such an instrument.

The method of radiofrequency resection of the meniscus is carried out as follows.

The method is carried out using a system of arthroscopic devices: an arthroscope, radiofrequency energizer, drainage system and other arthroscopic devices (shaver, ablator, arthroscopic clamp 15, etc.), and arthroscopic instrument 16 for radiofrequency resection of the meniscus. The system is designed to work in an electrically conductive liquid. For operations on joints, most often 0.9% NaCl is used.

The energizer-instrument system is designed to transmit radiofrequency oscillations to loop-electrode 6, arranged at the distal end of inner tube 3 of the arthroscopic instrument. Energy flows between the forward and backward parts of loop-electrode 6, which are located in a bipolar configuration. This creates a controlled, focused energy field to create plasma.

Under anesthesia, after processing the surgical field, arthroscopic ports are installed, into one of those ports, an arthroscope is inserted, and into the other port, there is arranged the arthroscopic instrument for radiofrequency resection of the meniscus when the outer tube (FIG. 12, FIG. 16) is in its closed position, and as soon as the instrument has been already located in the joint cavity, it is transferred to the open (FIG. 11, FIG. 15) position (according to the first and second variants of the instrument). After identification of damaged area 17 of the meniscus, while electrode-loop 6 is approaching the "target tissue", which is meniscus 18 of the knee joint, the process of molecular dissociation occurs. The state of plasma minimizes damage to the surrounding tissues of the surgical field, and the energy of radio-frequency oscillations, due to the shape of loop-electrode 6, takes an a form of a "blade", which allows carrying out high-precision discission 19 of the meniscus tissue, prevents excessive destruction of the meniscus tissue and surrounding tissues, as well as deformation of the meniscus. After performing the resection, the instrument is transferred to its closed position (FIG. 12, FIG. 16) (according to the first and second variants of the instrument) and removed from the joint. As a result, this configuration of the instrument allows obtaining one dissected fragment 20 of the meniscus, which can be evacuated from the joint cavity in full using an arthroscopic clamp 16 or destroyed using a shaver or ablator.

When provided with such an arthroscopic instrument, the resource of surgical support increases by reducing the need for the use of such instruments as a shaver, a cutting device, and an ablator.

An example of the implementation of the method.

Figure 20:
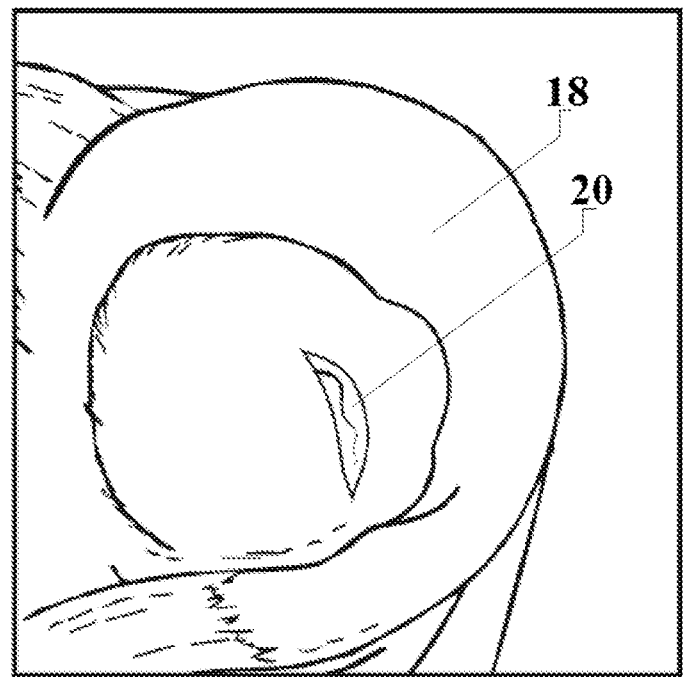
FIG. 20 shows the cavity of the knee joint with one separate damaged fragment resected from the meniscus.
Figure 21:
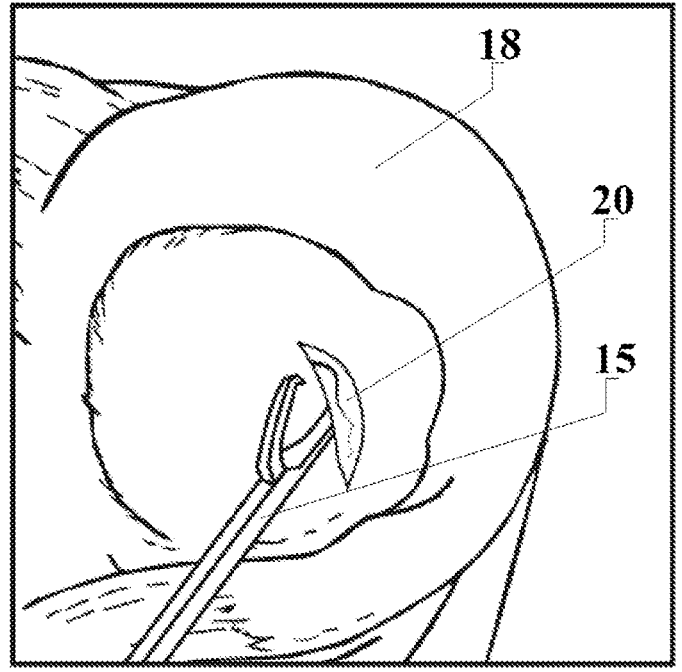
FIG. 21 shows the evacuating procedure of the meniscus resected damaged fragment with the use of an arthroscopic clamp.

Under anesthesia, after processing the surgical field with an antiseptic, two ports are installed into the knee joint in traditional places. A camera is inserted into the first port, and an arthroscopic instrument is inserted into the second port when the distal end of inner tube 3 (FIG. 12, FIG. 16) is in the closed position. After introducing the instrument, the distal end of inner tube 3 is moved to the open position by turning distal manipulator 10 (FIG. 11, FIG. 15). The damaged area 17 of the meniscus is identified. Resection of the damaged area 17 of the meniscus is carried out by pressing "start" button 2, this action entails transferring of high-frequency energy to loop-electrode 6 and forming localized plasma on the surface thereof. On bringing loop-electrode 6 closer to the surface of meniscus 18 and controlling the plane by loop-electrode 6 arrangement relative to the surface of meniscus 18 with the help of proximal manipulator 14, a high-precision discission 19 is made, as a result of which one resected damaged meniscus fragment 20 is obtained (FIG. 20). By turning distal manipulator 10, the distal end of inner tube 3 is transferred to the closed position, and the instrument is removed from the joint. The resected damaged fragment 20 is evacuated from the knee joint with an arthroscopic clamp 15 (FIG. 21). With the help of an aspiration system, aspiration opening 4 or aspiration tube 9, bubbles and low molecular weight products of decomposition arising from the process of molecular dissociation of the meniscus tissue are evacuated from the joint, improving the visualization of the surgical field.

The claimed arthroscopic instrument increases the resource of surgical support for arthroscopic operations, in particular, reduces the need to replace the instrument inserted into the joint, since it functions as a cutting device and an ablator at the same time, it significantly reduces the need to repeat resection cycles, and that is why, the level of trauma of the joint tissues, and also it increases resection accuracy. Target tissue resection process is possible due to molecular dissociation during transmission of radiofrequency energy to the target tissue in the form of plasma, at its volume controlled using an energizer console. The shape of the blade in the form of a loop increases the accuracy of the resection of the target tissue, which gives the ability to control the quality of the resection procedure more effectively. At the instrument distal end, the outer tube protects the inner tube, which includes a loop-electrode in it, from mechanical contact with soft tissues when the instrument is in the joint.

The instrument can be made disposable due to the simplicity of the design. This negates the need to waste additional resources for re-sterilization, and essentially eliminates the need in using lots of types of arthroscopic cutting devices, which gradually grow blunt, worn out, and require storage and re-sterilization.

The dimensions of the astroscopic instrument, namely, the diameter of the distal end of the instrument and the tubes thereof are adapted to the size of an arthroscopic port and do not exceed 5 mm.

The claimed instrument has improved visualization during surgery, since, in contrast to a cutting device, because of resection, the amount and volume of the dissected parts of the target tissue decreases, which event facilitates the procedure of their evacuation and improves visualization. In this case, the visualization is also improved due to the availability of an aspiration channel for aspiration of bubbles arising because of the process of molecular dissociation.

The invention claimed is:

1. A method for radiofrequency resection of a damaged area of a meniscus carried out by a system of arthroscopic devices comprising an optical device, the method comprising the steps of:

making at least two arthroscopic ports into a knee joint being treated by making a cut, inserting the optical device into one of the at least two arthroscopic ports, identifying the damaged area of the meniscus, inserting an arthroscopic cutting instrument into the cut through the other of the at least two arthroscopic ports, wherein the arthroscopic cutting instrument includes: a handle including a distal end and proximal end; an outer tube connected to the distal end of the handle, the outer tube includes a proximal end, a distal end, and a beveled tip located at the distal end of the outer tube; an inner tube having a proximal end and a distal end, the inner tube is located inside the outer tube and is connected to the distal end of the handle; the distal and of the inner tube includes an electrode opening and an aspiration opening, a loop-electrode rigidly connected to the inner tube, the loop-electrode is connected to the electrode opening, the loop-electrode is connected to a power cable, the power cable is located inside the handle and goes out of the handle at the proximal end of the handle, the power cable is connected to a radio frequency generator, a drainable tube located inside the inner tube and connected to the aspiration opening, the drainable tube goes thru proximal end of the handle, an aspiration tube connected to the drainable tube and to an aspiration system, a starting device; and a distal manipulator, the distal manipulator is located at the handle and is configured to control a linear movement of the outer tube from a first position, in which the inner tube and the loop-electrode are placed inside the outer tube to a second position, in which the inner tube and loop-electrode protrude from the outer tube;

inserting the distal end of the inner tube into the knee joint being treated when the inner tube is at the first position, turning the distal manipulator to move the outer tube into the second position, energizing the loop-electrode by transferring high-frequency forming a localized plasma on a surface of the loop-electrode;

cutting the damaged area of the meniscus with the localized plasma of the loop-electrode;

removing the damaged area of the meniscus with the localized plasma of the loop-electrode, turning the distal manipulator to move the outer tube into the first position, removing the arthroscopic cutting instrument from the knee joint, removing debris from the damaged area by using the aspiration tube, removing the damaged area of the meniscus from the knee joint using an arthroscopic clamp, and suturing the arthroscope port.

2. An arthroscopic instrument for radiofrequency resection of a damaged area of a meniscus comprising:

a handle including a proximal end, a distal end, a distal manipulator, and a start button;

an outer tube connected to the distal end of the handle, the outer tube includes a proximal end, a distal end, and a beveled tip located at the distal end of the outer tube;

an inner tube located inside the outer tube, the inner tube is connected to the distal end of the handle, the inner tube having a proximal end and a distal end, the distal end of the inner tube having an electrode opening and an aspiration opening;

a loop-electrode located inside the inner tube and rigidly connected to the inner tube, the loop-electrode is connected to the electrode opening, the loop-electrode is connected to a power cable, the power cable is located inside the handle and goes out of the handle at the proximal end of the handle, the power cable is connected a radio-frequency generator;

a starting device; and a distal manipulator, the distal manipulator is located at the handle and is configured to control a linear movement of the outer tube from a first position, in which the inner tube and the loop-electrode are placed inside the outer tube to a second position, in which the inner tube and loop-electrode protrude from the outer tube;

a drainable tube located inside the inner tube and connected to the aspirating opening, the drainable tube goes thru the proximal end of the handle, an aspiration tube connected to the drainable tube and to an aspiration system, wherein the distal manipulator is configured to control a linear movement of the outer tube from the first position, in which the inner tube and the loop-electrode are placed inside the outer tube to the second position, in which the inner tube and loop-electrode protrude from the outer tube; and wherein the outer tube has a diameter of up to 5 mm.

3. The arthroscopic instrument according to claim 2, wherein the tip of the outer tube has a beveled tip at an angle between 30 to 60 degrees.

4. An arthroscopic instrument for radiofrequency resection of a damaged area of a meniscus, comprising:

a handle including a proximal end, a distal end, a distal manipulator, a proximal manipulator, and a start button;

an outer tube connected to the distal end of the handle, the outer tube includes a proximal end and a distal end, and a beveled tip located at the distal end of the outer tube, the beveled tip has an angle between 30 to 60 degrees;

an inner tube located inside the outer tube, the inner tube includes a proximal end and a distal end, the inner tube is connected to the distal end of the outer tube, the distal end of the inner tube includes an electrode opening and an aspiration opening;

a loop-electrode is located inside the inner and is rigidly connected to the inner tube, the loop-electrode is connected to the electrode opening, the loop-electrode is connected to a power cable, the power cable is located inside the handle and goes out of the handle at the proximal end of the handle, the power cable is connected a connected to a radio frequency generator;

a drainage tube located inside the inner tube and goes thru the handle and then out of the handle by proximal end of the handle, an aspiration tube connected to the drainable tube and to an aspiration system; and a proximal manipulator located on the proximal end of the handle, the proximal manipulator is configured to rotate the inner tube inside the outer tube;

a distal manipulator located at the distal end of the handle, the distal manipulator is configured to linearly move the outer tube from a first position, in which the inner tube and the loop-electrode are placed inside the outer tube to a second position, in which the inner tube and loop-electrode protrude from the outer tube, and wherein the outer tube has a diameter of up to 5 mm.

* * * * *